United States Patent
Kyuuko et al.

(10) Patent No.: US 6,504,069 B1
(45) Date of Patent: Jan. 7, 2003

(54) PROCESS FOR PRODUCING DIMETHYLTETRALIN

(75) Inventors: Youichi Kyuuko, Ibaraki-ken (JP); Norio Fushimi, Ibaraki-ken (JP); Makoto Takagawa, Ibaraki-ken (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/504,042

(22) Filed: Feb. 14, 2000

(30) Foreign Application Priority Data

Feb. 22, 1999 (JP) .......... 11-043455
Feb. 22, 1999 (JP) .......... 11-043456

(51) Int. Cl.$^7$ .............................. C07C 13/28
(52) U.S. Cl. ............. 585/410; 585/400; 585/411
(58) Field of Search ............... 585/400, 410, 585/411

(56) References Cited

U.S. PATENT DOCUMENTS

| | | | |
|---|---|---|---|
| 3,244,758 A | 4/1966 | Eberhardt | 585/320 |
| 3,775,496 A | 11/1973 | Thompson | 585/320 |
| 3,775,500 A | * 11/1973 | Thompson | 585/320 |
| 3,840,609 A | 10/1974 | Oka et al. | |
| 3,843,737 A | 10/1974 | Chong | 585/320 |
| 3,997,616 A | 12/1976 | Tokashiki et al. | 585/411 |
| 4,950,825 A | 8/1990 | Sikkenga et al. | 585/320 |
| 5,008,479 A | 4/1991 | Abe et al. | |
| 5,030,781 A | 7/1991 | Sikkenga et al. | 585/320 |
| 5,396,008 A | 3/1995 | Ozawa et al. | 585/411 |
| 5,401,892 A | 3/1995 | Sikkenga et al. | 585/320 |

FOREIGN PATENT DOCUMENTS

| | | |
|---|---|---|
| JP | 48-67261 | 9/1973 |
| JP | 49-11385 | 3/1974 |
| JP | 49-93348 | 9/1974 |
| JP | 49-134634 | 12/1974 |
| JP | 50-89353 | 7/1975 |
| JP | 1-503389 | 11/1989 |
| JP | 2-96540 | 4/1990 |
| JP | 3-500052 | 1/1991 |
| JP | 6-56709 | 3/1994 |
| JP | 8-40946 A | 2/1996 |
| WO | WO88/09318 | 12/1988 |
| WO | WO89/12612 | 12/1989 |

* cited by examiner

*Primary Examiner*—Walter D. Griffin
(74) *Attorney, Agent, or Firm*—Antonelli, Terry, Stout & Kraus, LLP

(57) ABSTRACT

5-Tolyl-pent-2-ene is cyclized in liquid phase in the present of an aliphatic hydrocarbon to produce the corresponding dimethyltetralin. The use of the aliphatic hydrocarbon effectively prevents a side reaction such as dimerization of 5-tolyl-pent-2-ene to provide dimethyltetralin in a high yield. Also, 5-tolyl-pent-2-ene is cyclized in liquid phase or vapor phase in the presence of a catalyst comprising a carrier supporting sulfate ions to produce the corresponding dimethyltetralin. The catalyst supporting sulfate ions shows a high catalytic activity event at low temperatures. Therefore, the cyclization of 5-tolyl-pent-2-ene is conducted in a wide temperature range from low temperatures to high temperatures.

12 Claims, No Drawings

PROCESS FOR PRODUCING DIMETHYLTETRALIN

BACKGROUND OF THE INVENTION

The present invention relates to a process for producing dimethyltetralin useful as a raw material of naphthalenedicarboxylic acid used for producing plastics such as polyesters.

Dimethyltetralin is converted to dimethylnaphthalene by dehydrogenation. Therefore, dimethyltetralin is a very important compound useful as a raw material of naphthalenedicarboxylic acid which is used for the production of plastics such as polyesters. For instance, polyethylene 2,6-naphthalate produced from 2,6-naphthalenedicarboxylic acid and ethylene glycol is suitably used for the production of films or fibers having more excellent heat resistance and mechanical properties than those of polyethylene terephthalate. Naphthalenedicarboxylic acid used as a raw material of plastics has been required to be isomerically highly pure. Therefore, dimethylnaphthalene used as a raw material of naphthalenedicarboxylic acid is also required to be isomerically highly pure. More specifically, the dimethylnaphthalene includes ten isomers, i.e., 1,2-1,3-, 1,4-, 1,5-, 1,6-, 1,7-, 1,8-, 2,3-, 2,6- and 2,7-isomers, according to the positions of two methyl groups. If an isomer is to be used as a raw material of naphthalenedicarboxylic acid, it is required to be isomerically highly pure, i.e., required to be free from the other isomers.

Dimethylnaphthalene is obtained by separation of high-boiling fractions from petroleum refining, separation of coal tars, alkylation of naphthalene, reaction of alkyl benzene and olefin, etc.

Since dimethylnaphthalene contained in high-boiling fractions from petroleum refining or coal tars is a mixture of isomers, an isomerization step or a complicated isomer-separating step is required to separate a desired single isomer of dimethylnaphthalene from the isomeric mixture. Based on easiness of interconversion between isomers, 10 isomers of dimethylnaphthalene (hereinafter may be referred to as "DMN") are classified into the following four groups. Although the isomers are relatively easily isomerized to another in the same group, isomerization between different groups is difficult to take place. Further, in addition to the great difficulty in separating an aimed dimethylnaphthalene isomer from the other isomers, it is very difficult to separate and recover the aimed isomer in a high purity from the high-boiling fractions from petroleum refining and coal tars, because the fractions and coal tars actually contain many components other than dimethylnaphthalene isomers, Group A: 1,5-DMN, 1.6-DMN and 2,6-DMN Group B: 1,7-DMN, 1.8-DMN and 2,7-DMN Group C: 1,3-DMN, 2,3-DMN and 1,4-DMN Group D: 1,2-DMN Alkylation of naphthalene is performed usually in the presence of a solid acid catalyst such as zeolite and silica alumina. In this method, monomethylnaphthalene, trimethylnaphthalene, etc. are by-produced with dimethylnaphthalene, and therefore, the selectivity to dimethylnaphthalene is not so high. In addition, the resultant dimethylnaphthalene is a mixture of many isomers. Thus, like the separation of high-boiling fractions from petroleum refining and the separation of coal tars, the alkylation of naphthalene fails to produce a specific dimethylnaphthalene isomer in a high yield.

To remedy the above problems, there have been proposed methods of producing a specific dimethylnaphthalene isomer from alkyl benzene and olefin via multiple steps. For instance, Japanese Patent Application Laid-Open No. 2-96540 discloses a method of producing 2,6-dimethylnaphthalene from m-xylene, propylene and carbon monoxide. U.S. Pat. No. 5,008,479 discloses a method of producing 2,6-dimethylnaphthalene from toluene, butene and carbon monoxide.

Japanese Patent Application Laid-Open No. 49-134634 discloses a method of producing 5-(o-tolyl)-pent-2-ene from o-xylene and butadiene; Japanese Patent Application Laid-Open No. 50-89353 discloses a method of producing 1,5-dimethyltetralin by cyclizing 5-(o-tolyl)-pent-2-ene; and Japanese Patent Application Laid-Open No. 48-67261 discloses a method of producing 1,5-dimethylnaphthalene by dehydrogenating 1,5-dimethyltetralin. By combining these teachings, isomerically highly pure 1,5-dimethylnaphthalene can be obtained from o-xylene and butadiene.

Japanese Patent Application Laid-Open No. 1-503389 discloses a method of isomerizing 1,5-dimethylnaphthalene to obtain a mixture of 1,5-dimethylnaphthalene, 1,6-dimethylnaphthalene and 2,6-dimethylnaphthalene, and then separating highly pure 2,6-dimethylnaphthalene by crystallization from the mixture. The proposed method utilizes the isomerization and crystallization between the three dimethylnaphthalene isomers belonging to the same isomerization group mentioned above, and therefore, can be carried out more advantageously as compared to the isomerization and crystallization between isomers belonging to different groups. Many studies have been made on the development of industrial production methods of 2,6-dimethylnaphthalene, because it is the most notable isomer as a raw material for 2,6-naphthalenedicarboxylic acid.

A method of producing dimethylnaphthalene from xylene and butadiene comprises a step of alkenylating one of two methyl groups of xylene to obtain 5-tolyl-pent-2-ene, a step of cyclizing 5-tolyl-pent-2-ene to obtain dimethyltetralin, a step of dehydrogenating dimethyltetralin to obtain dimethylnaphthalene, a step of isomerizing dimethylnaphthalene, and a step of crystallizing followed by separation.

Regarding the production of dimethyltetralin by cyclization of 5-(oolyl)-pent-2-ene, Japanese Patent Application Laid-Open No. 49-93348 proposes to carry out the cyclization at 180 to 350° C. in liquid phase using a solid phosphoric acid.

Japanese Patent Application Laid-Open No. 3-500052 teaches that a cyclization at 120 to 250° C. in liquid phase in the presence of a catalyst such as a platinum- or copper-modified ultra-stabilized Y-type zeolite (USY) produces dimethyltetralin in a yield of 95% or more. It also discloses, as preferred solvents optionally used, a solvent having a boiling point of about 270° C. or higher, exemplified by paraffin such as tetradecane, aromatic hydrocarbon such as anthracene and a mixture thereof.

Japanese Patent Application Laid-Open No. 6-56709 discloses that dimethyltetralin can be obtained in a high yield by vapor-phase cyclization at 100 to 400° C. using a catalyst comprising mordenite and silica to completely prevent the dimerization of 5-tolyl-pent-2-ene. However, the vapor-phase cyclization requires several considerations in achieving a sufficiently high reaction temperature, using a considerably large amount of diluent, reducing reaction pressure, etc.

Japanese Patent Publication No. 49-11385 teaches that dimethyltetralin can be obtained in a high yield by carrying out the cyclization at lower temperatures in the absence of solvent using a cation exchange resin as a catalyst. However, since the catalyst is effective only up to 150° C., the working temperature range of the catalyst is limited to narrow range. In addition, since cation exchange resins are generally expensive, the proposed method is costly disadvantageous for industrial use.

As described above, dimethyltetralin can be produced by cyclizing 5-tolyl-pent-2-ene which is obtained by alkenylating a side chain of xylene with butadiene, and then dehydrogenating the resultant dimethyltetralin. When 5-tolyl-pent-2-ene is cyclized to dimethyltetralin in liquid phase, dimerization of 5-tolyl-pent-2-ene is likely to occur, thereby failing to obtain dimethyltetralin in a high yield. Also, when an aromatic hydrocarbon is used as a solvent for the cyclization in the presence of a catalyst conventionally used, the selectivity to dimethyltetralin is low due to the reaction of 5-tolyl-pent-2-ene with the aromatic hydrocarbon. It is reported that vapor-phase cyclization of 5-tolylpent-2-ene can prevent the production of high-boiling compounds. However, the vapor-phase cyclization known in the art should be carried out under limited reaction conditions because sufficiently high temperature is required.

Although a high yield is obtained in the conventional methods where 5-tolyl-pent-2-ene is cyclized to the corresponding dimethyltetralin, the working temperature range of the catalyst is narrow. Therefore, when the cyclization is carried out at higher temperatures or lower temperatures, the use of expensive cation exchange resins is needed.

Accordingly, it is an object of the present invention to provide a process for producing dimethyltetralin in a high yield from 5-tolyl-pent-2-ene in industrially advantageous manner.

Another object of the present invention is to provide a process for cyclizing 5-tolyl-pent-2-ene to the corresponding dimethyltetralin at a temperature as low as possible, thereby producing dimethyltetralin in industrially advantageous manner.

SUMMARY OF THE INVENTION

As a result of extensive studies of the inventors for solving the above problems, it has been found that the presence of an aliphatic hydrocarbon in liquid-phase cyclization of 5-tolyl-pent-2-ene effectively prevents the side reaction, i.e., dimerization of 5-tolyl-pent-2-ene and allows the cyclization to proceed nearly quantitatively, thereby enabling to obtain the corresponding dimethyltetralin in a high conversion and a high yield. Since the aliphatic hydrocarbon is commercially easily available and readily reused by distillation, dimethyltetralin is obtained in industrially advantageous manner. The inventors have further found that the cyclization of 5-tolyl-pent-2-ene proceeds nearly quantitatively in the presence of a catalyst comprising a carrier supporting sulfate ions to produce the corresponding dimethyltetralin in high conversion and high yield due to high catalytic activity even at lower temperatures. Since the catalyst comprising a carrier supporting sulfate ions are cheap and easy to prepare, dimethyltetralin is produced in-industrially advantageous manner. The present invention has been accomplished based on these findings.

Thus, in a first aspect of the present invention, there is provided a process for producing dimethyltetralin by a liquid-phase cyclization of 5-tolyl-pent-2-ene in the presence of aliphatic hydrocarbon.

In a second aspect of the present invention, there is provided a process for producing dimethyltetralin by cyclizing 5-tolyl-pent-2-ene in the presence of a catalyst supporting sulfate ion.

DETAILED DESCRIPTION OF THE INVENTION

As described above, the starting material, 5-tolyl-pent-2-ene, used in the present invention is produced by alkenylating a side chain of xylene with butadiene. 5-Tolyl-pent-2-ene includes three isomers, 5-(o-tolyl)-pent-2-ene, 5-(m-tolyl)-pent-2-ene and 5-(p-tolyl)-pent-2-ene, corresponding to the xylene isomer to be used. Any of the isomers may be used in the present invention.

(I) First Production Method

In the first production method of dimethyltetralin, the cyclization is performed in the presence of a catalyst. The catalyst may include solid acids and liquid acids such as sulfuric acid and phosphoric acid which may be impregnated into a carrier such as alumina, silica, titania, zirconia, zeolite, silica-alumina, silica-zirconia and silica-titania. Preferred are solid acids such as zeolite, silica-alumina, silica-zirconia, silica-titania, etc.

The aliphatic hydrocarbons used in the first production method referably have 6 to 12 carbon atoms, and may include hexane, heptane, nonane, decane, cyclohexane and cyclodecane. The amount of the aliphatic hydrocarbon used as a solvent is not particularly restricted, and preferably an excess amount to the starting 5-tolyl-pent-2-ene, for example, 2 to 20 g per 1 g of 5-tolyl-pent-2-ene is used because the production of a high-boiling compound, i.e., a dimer of 5-tolyl-pent-2-ene is effectively minimized to enhance the selectivity to dimethyltetralin.

The reaction temperature for cyclizing 5-tolyl-pent-2-ene is not particularly restricted and may be appropriately determined according to the activity of the catalyst used. Preferably, the cyclization is conducted at 100 to 300° C. When the reaction temperature is much higher than a catalytically optimum temperature, the resultant dimethyltetralin includes many isomers to result in failure to obtain a desired dimethyltetralin isomer in a high yield. When the reaction temperature is too low, dimethyltetralin is not obtained in a high yield due to decreased conversion of 5-tolyl-pent-2-ene. In the first production method, the cyclization is carried out at a pressure at which the starting materials are held in liquid phase. The cyclization may be-carried out under pressure by nitrogen to maintain the reaction system in liquid phase. Preferred reaction pressure is 0.1 to 2 MPa.

The type of the reaction apparatus for the liquid-phase cyclization of 5-tolyl-pent-2-ene is not particularly restricted. Any known type of apparatuses such as fixed bed reactor, moving bed reactor and fluidized bed reactor may be used in the present invention. When the reaction is carried out continuously, a fixed bed flow reactor is preferable in view of facilitating the operations. The feeding rate of 5-tolyl-pent-2-ene per unit weight of the catalyst varies depending upon the type of reactor. For instance, when a fixed bed flow reactor is used, the liquid hourly space velocity (LHSV) is 0.01 to 5 $hr^{-1}$, preferably 0.1 to 1 $hr^{-1}$.

After completion of the cyclization, dimethyltetralin is separated from the reaction liquid by distillation, etc., and then used for producing naphthalenedicarboxylic acid through dimethylnaphthalene in known methods.

Japanese Patent Application Laid-Open No. 49-93348 referred to above teaches that dimethyltetralin can be produced by cyclizing 5-(o-tolyl)-pent-2-ene in liquid phase in the presence of solid phosphoric acid using a diluent such as hexane, cyclohexane, octane, dimethyloctane, benzene, toluene, xylene, tetralin and dimethyltetralin. However, in any of the working examples, neither solvent nor diluent is actually used. Since the aliphatic hydrocarbons and aromatic hydrocarbons are taught equivalent to each other as the diluent, it cannot be expected from Japanese Patent Application Laid-Open No. 49-93348 that the use of aliphatic hydrocarbon as a solvent produces results superior to the use of aromatic hydrocarbon in the liquid-phase cyclization of 5-(o-tolyl)-pent-2-ene. Also, Japanese Patent Application Laid-Open No. 3-500052 teaches that the yields of dimethyltetralin from 5-(o-tolyl)-pent-2-ene are 92% or higher in any of the working examples. However, in considering insufficient precision of gas chromatographic technique on high-boiling components at the time the invention described therein was made, it may be presumed that the taught dimethyltetralin contained in negligible amount of 5-(o-tolyl)-pent-2-ene dimer.

(II) Second Production Method

The catalyst used in the second production method comprises a carrier supporting sulfate ions. The source of sulfate ions is a compound capable of forming sulfate ions on a carrier by supporting treatment and subsequent calcining treatment, and may be sulfuric acid, ammonium sulfate, etc. Any kinds of carriers may be used as far as the carrier supports sulfate ions dispersedly, and metal oxides such as titanium oxide, zirconium oxide, aluminum oxide, silica, physical mixtures thereof and composite oxides thereof may be preferably used. The carrier may be used in the form of powder or shaped article. Sulfate ions may be supported 0.01 to 0.5 part by weight, preferably 0.02 to 0.3 part by weight as $SO_4$ on 1 part by weight of the carrier. The preparation method of the catalyst is not specifically limited as far as sulfate ions are supported on the carrier well dispersedly. For example, the catalyst may be prepared by impregnating a carrier with aqueous solution of sulfuric acid, drying and then calcining.

The cyclization temperature of 5-tolyl-pent-2-ene is 50 to 400° C., preferably 70 to 300° C. When the temperature is higher than the above range, a mixture of many dimethyltetralin isomers will be obtained, thereby failing to obtain a specific dimethyltetralin isomer in high yield. A temperature lower than the above temperature range will decrease the conversion of 5-tolyl-pent-2-ene, thereby reducing the yield of dimethyltetralin.

The catalyst used in the second production method is unique for solid acid catalysts in that it shows, even at lower temperatures in liquid or vapor phase, significantly high catalytic activity enough to produce dimethyltetralin from 5-tolyl-pent-2-ene in high yield. Therefore, by using such a catalyst, the cyclization is carried out in a wide temperature range from lower to higher temperatures in liquid phase or vapor phase.

Liquid-phase cyclization is carried out at a pressure at which the starting materials are held in liquid phase. Although the cyclization may be conducted under atmospheric pressure, the pressure may be increased by nitrogen to maintain the reaction system in liquid phase. The liquid-phase cyclization may be carried out without using a solvent, or using a solvent, preferably hydrocarbon such as hexane, cyclohexane, heptane, octane, decalin, benzene, toluene, xylene, tetralin, dimethyltetralin, etc. By the use of the catalyst supporting sulfate ions, the drawback of aromatic hydrocarbon as the solvent to reduce the selectivity to dimethyltetralin in the known methods is removed. Therefore, in the second production method, dimethyltetralin is obtained in a high yield even when aromatic hydrocarbon is used in the liquid-phase cyclization of 5-tolyl-pent-2-ene. The amount of the solvent may be not particularly limited, and suitably determined depending on reaction pressure, reaction temperature, kinds of solvent, space velocity, etc. Preferably, the amount is 1 to 20 g per 1 g of 5-tolyl-pent-2-ene.

Vapor-phase cyclization is carried out while holding the starting materials substantially in vapor phase. Although the vapor-phase cyclization may be conducted under atmospheric pressure, a diluent may be used and the cyclization may be carried out under reduced pressure to maintain the vapor phase. The diluent is not strictly limited as far as it is inert to the reaction, and may be nitrogen, hydrogen, helium, argon, hexane, cyclohexane, heptane, octane, decalin, benzene, toluene, xylene, tetralin, dimethyltetralin, etc.

The type of the reaction apparatus for the second production method is not particularly restricted, and any known type of apparatuses such as fixed bed reactor, moving bed reactor and fluidized bed reactor may be used. When the reaction is carried out continuously, a fixed bed flow reactor is preferable in view of facilitating the operations. The feeding rate of 5-tolyl-pent-2-ene per unit weight of the catalyst varies depending upon the type of reactor. For instance, when a fixed bed flow reactor is used, the liquid hourly space velocity (LHSV) is 0.01 to 5 $hr^{-1}$, preferably 0.1 to 1 $hr^{-1}$.

After completion of the cyclization, dimethyltetralin is separated from the reaction liquid by distillation, etc., and then used for producing naphthalenedicarboxylic acid through dimethylnaphthalene in known methods.

The present invention will be described in further detail by way of the following Examples and Comparative Examples. However, it should be noted that the present invention is not intended to be limited thereto.

In the following Examples and Comparative Examples, 10 g of each catalyst were packed into a quartz reaction tube with 20 mm inner diameter.

Example 1

Silica-alumina catalyst ($SiO_2$=66.5%, $Al_2O_3$=25.1%) was packed into a reaction tube, and the inner pressure was adjusted to 20 MPa by nitrogen. The cyclization was conducted at 170° C. by feeding 5-(o-tolyl)-pent-2-ene and heptane into the reaction tube at feeding rates of 5 g/hr and 45 g/hr, respectively. The results of gas chromatographic analysis of the resultant reaction solution showed that the conversion of 5-(o-tolyl)-pent-2-ene was 100% and the selectivity to dimethyltetralin was 94.5% (molar basis, and the same is applied hereinafter).

Example 2

The same silica-alumina catalyst as used in Example 1 was packed into a reaction tube, and the inner pressure was adjusted to 20 MPa by nitrogen. The cyclization was conducted at 170° C. by feeding 5-(o-tolyl)-pent-2-ene and heptane into the reaction tube at feeding rates of 5 g/hr and 20 g/hr, respectively. The results of gas chromatographic analysis of the resultant reaction solution showed that the conversion of 5-(o-tolyl)-pent-2-ene was 100% and the selectivity to dimethyltetralin was 93.5%.

Example 3

The cyclization was conducted in the same manner as in Example 2 except that 5-(m-tolyl)-pent-2-ene was used. The results of gas chromatographic analysis of the resultant reaction solution showed that the conversion of 5-(m-tolyl)-pent-2-ene was 100% and the selectivity to dimethyltetralin was 94.0%.

Example 4

The cyclization was conducted in the same manner as in Example 2 except that 5-(p-tolyl)-pent-2-ene was used. The results of gas chromatographic analysis of the resultant reaction solution showed that the conversion of 5-(p-tolyl)-pent-2-ene was 100% and the selectivity to dimethyltetralin was 93.2%.

Example 5

The same silica-alumina catalyst as used in Example 1 was packed into a reaction tube, and the inner pressure was adjusted to 20 MPa by nitrogen.

The cyclization was conducted at 170° C. by feeding 5-(o-tolyl)-pent-2-ene and heptane into the reaction tube at feeding rates of 5 g/hr and 10 g/hr, respectively. The results of gas chromatographic analysis of the resultant reaction solution showed that the conversion of 5-(o-tolyl)-pent-2-ene was 100% and the selectivity to dimethyltetralin was 92.0%.

Example 6

The same silica-alumina catalyst as used in Example 1 was packed into a reaction tube, and the inner pressure was adjusted to 20 MPa by nitrogen. The cyclization was conducted at 170° C. by feeding 5-(o-tolyl)-pent-2-ene and decane into the reaction tube at feeding rates of 5 g/hr and 45 g/hr, respectively. The results of gas chromatographic analysis of the resultant reaction solution showed that the conversion of 5-(o-tolyl)-pent-2-ene was 100% and the selectivity to dimethyltetralin was 94.3%.

Example 7

Mordenite catalyst (Si/Al=200) was packed into a reaction tube, and the inner pressure was adjusted to 20 MPa by nitrogen. The cyclization was conducted at 170° C. by feeding 5-(o-tolyl)-pent-2-ene and decane into the reaction tube at feeding rates of 5 g/hr and 45 g/hr, respectively. The results of gas chromatographic analysis of the resultant reaction solution showed that the conversion of 5-(o-tolyl)-pent-2-ene was 100% and the selectivity to dimethyltetralin was 93.0%.

Comparative Example 1

The same silica-alumina catalyst as used in Example 1 was packed into a reaction tube, and the inner pressure was adjusted to 20 MPa by nitrogen. The cyclization was conducted at 170° C. in the absence of solvent by feeding 5-(o-tolyl)-pent-2-ene into the reaction tube at a feeding rate of 5 g/hr. The results of gas chromatographic analysis of the resultant reaction solution showed that the conversion of 5-(o-tolyl)-pent-2-ene was 100% and the selectivity to dimethyltetralin was 89.7%.

Comparative Example 2

The same silica-alumina catalyst as used in Example 1 was packed into a reaction tube, and the inner pressure was adjusted to 20 MPa by nitrogen. The cyclization was conducted at 170° C. by feeding 5-(o-tolyl)-pent-2-ene and toluene into the reaction tube at feeding rates of 5 g/hr and 45 g/hr, respectively. The results of gas chromatographic analysis of the resultant reaction solution showed that the conversion of 5-(o-tolyl)-pent-2-ene was 100% and the selectivity to dimethyltetralin was 88.7%.

Comparative Example 3

The same silica-alumina catalyst as used in Example 1 was packed into a reaction tube, and the inner pressure was adjusted to 20 MPa by nitrogen. The cyclization was conducted at 170° C. by feeding 5-(o-tolyl)-pent-2-ene and oxylene into the reaction tube at feeding rates of 5 g/hr and 45 g/hr, respectively. The results of gas chromatographic analysis of the resultant reaction solution showed that the conversion of 5-(o-tolyl)-pent-2-ene was 100% and the selectivity to dimethyltetralin was 87.5%.

Example 8

A catalyst was prepared by drying 200 g of a shaped body of zirconium oxide impregnated with an aqueous solution of 25 g ammonium sulfate in 100 g water at 100° C., and calcining the dried body at 500° C. for 3 hours. The catalyst thus prepared was packed into a reaction tube, and the cyclization was carried out at 70° C. under atmospheric pressure by feeding the starting 5-(oolyl)-pent-2-ene into the reaction tube at a feeding rate of 5 g/hr. The results of gas chromatographic analysis on the reaction liquid are shown in Table 1.

Example 9

The same catalyst as used in Example 8 was packed into a reaction tube, and the cyclization was carried out at 70° C. under atmospheric pressure by feeding the starting 5-(o-tolyl)-pent-2-ene and heptane into the reaction tube at feeding rates of 5 g/hr and 20 g/hr, respectively. The results are shown in Table 1.

Example 10

A catalyst was prepared by drying 40 g of a shaped body of titanium oxide impregnated with an aqueous solution of 5 g sulfuric acid in 20 g water at 110° C., and calcining the dried body at 500° C. for 3 hours. The catalyst thus prepared was packed into a reaction tube, and the cyclization was carried out at 70° C. under atmospheric pressure by feeding the starting 5-(o-tolyl)-pent-2-ene and heptane into the reaction tube at feeding rates of 5 g/hr and 20 g/hr, respectively. The results are shown in Table 1.

Example 11

A catalyst was prepared by drying 40 g of a shaped body of composite silica-alumina impregnated with an aqueous solution of 5 g sulfuric acid in 20 g water at 110° C., and calcining the dried body at 500° C. for 3 hours. The catalyst thus prepared was packed into a reaction tube, and the cyclization was carried out at 70° C. under atmospheric pressure by feeding the starting 5-(o-tolyl)-pent-2-ene and heptane into the reaction tube at feeding rates of 5 g/hr and 20 g/hr, respectively. The results are shown in Table 1.

Example 12

A catalyst was prepared by drying 200 g of a shaped body of zirconium oxide impregnated with an aqueous solution of 25 g ammonium sulfate in 100 g water at 110° C., and calcining the dried body at 500° C. for 3 hours. The catalyst thus prepared was packed into a reaction tube, and the cyclization was carried out at 170° C. under atmospheric pressure by feeding the starting 5-(otolyl)-pent-2-ene and nitrogen into the reaction tube at feeding rates of 5 g/hr and 120 cc/min. The results are shown in Table 1.

Example 13

A catalyst was prepared by drying 200 g of a shaped body of aluminum oxide impregnated with an aqueous solution of 25 g ammonium sulfate in 100 g water at 110° C., and calcining the dried body at 400° C. for 3 hours. The catalyst thus prepared was packed into a reaction tube, and the cyclization was carried out at 170° C. under atmospheric pressure by feeding the starting 5-(otolyl)-pent-2-ene and nitrogen into the reaction tube at feeding rates of 5 g/hr and 120 cc/min. The results are shown in Table 1.

Example 14

A catalyst was prepared by drying 200 g of a shaped body of aluminum oxide impregnated with an aqueous solution of 25 g ammonium sulfate in 100 g water at 110° C., and calcining the dried body at 500° C. for 3 hours. The catalyst thus prepared was packed into a reaction tube, and the cyclization was carried out at 170° C. under atmospheric pressure by feeding the starting 5-(otolyl)-pent-2-ene and nitrogen into the reaction tube at feeding rates of 5 g/hr and 120 cc/min. The results are shown in Table 1.

Example 15

A catalyst was prepared by drying 200 g of a shaped body of zirconium oxide impregnated with an aqueous solution of 25 g ammonium sulfate in 100 g water at 110° C., and calcining the dried body at 500° C. for 3 hours. The catalyst thus prepared was packed into a reaction tube, and the cyclization was carried out at 70° C. under atmospheric pressure by feeding the starting 5-(otolyl)-pent-2-ene and heptane into the reaction tube at feeding rates of 5 g/hr and 20 g/hr, respectively. The results are shown in Table 1.

Example 16

A catalyst was prepared by drying 200 g of a shaped body of zirconium oxide impregnated with an aqueous solution of 25 g ammonium sulfate in 100 g water at 110° C., and calcining the dried body at 500° C. for 3 hours. The catalyst thus prepared was packed into a reaction tube, and the cyclization was carried out at 70° C. under atmospheric pressure by feeding the starting 5-(otolyl)-pent-2-ene and benzene into the reaction tube at feeding rates of 5 g/hr and 20 g/hr, respectively. The results are shown in Table 1.

Comparative Example 4

Strongly acidic perfluorinated ion exchange resin (NAFION manufactured by E. I. Du Pont) was packed into a reaction tube, and the cyclization was carried out at 120° C. under atmospheric pressure by feeding the starting 5-(o-tolyl)-pent-2-ene and heptane into the reaction tube at feeding rates of 5 g/hr and 20 g/hr, respectively. The results are shown in Table 1.

Comparative Example 5

Mordenite (Si/Al=200) was packed into a reaction tube, and the cyclization was carried out at 70° C. under atmospheric pressure by feeding the starting 5-(o-tolyl)-pent-2-ene and heptane into the reaction tube at feeding rates of 5 g/hr and 20 g/hr, respectively. The results are shown in Table 1.

Comparative Example 6

Silica-alumina ($SiO_2$=66.5%, $Al_2O_3$=25.1%) was packed into a reaction tube, and the cyclization was carried out at 70° C. under atmospheric pressure by feeding the starting 5-(o-tolyl)-pent-2-ene and heptane into the reaction tube feeding rates of 5 g/hr and 20 g/hr, respectively. The results are shown in Table 1.

TABLE 1

|  | Yield of DMT[*1] (mol %) | Unreacted OTP[*2] (mol %) | Selectivity to DMT[*1] (mol %) |
|---|---|---|---|
| Examples |  |  |  |
| 8 | 90.2 | 0 | 90.2 |
| 9 | 93.1 | 0 | 93.1 |
| 10 | 93.5 | 0 | 93.5 |
| 11 | 93.3 | 0 | 93.3 |
| 12 | 93.8 | 0 | 93.8 |
| 13 | 93.5 | 0 | 93.5 |
| 14 | 91.2 | 3.8 | 94.8 |
| 15 | 93.3 | 0 | 93.3 |
| 16 | 92.7 | 0 | 92.7 |
| Comparative Examples |  |  |  |
| 4 | 82.0 | 5.2 | 86.5 |
| 5 | 37.5 | 60.4 | 94.7 |
| 6 | 37.7 | 61.2 | 97.2 |

DMT[*1] is 1,5-dimethyltetralin.
OTP[*2] is 5-(o-tolyl)-pent-2-ene.

As seen from the above Examples, the liquid-phase cyclization of 5-tolyl-pent-2-ene in the presence of aliphatic hydrocarbon produces the corresponding dimethyltetralin in a high yield. Further, since the aliphatic hydrocarbon is commercially easily available and readily recycled by distillation, etc., dimethyltetralin is obtained in industrially advantageous manner by the present invention.

Also, as seen from Examples, since the catalyst supporting sulfate ions provides an extremely high conversion of the starting 5-(o-tolyl)-pent-2-ene and a high selectivity to dimethyltetralin, the aimed dimethyltetralin is obtained in a high yield. Also, since the resultant 1,5-dimethyltetralin is isomerically highly pure, the aimed dimethyltetralin isomer is obtained in high yield regardless of whether the cyclization is proceed in vapor phase or liquid phase. In addition, since the catalyst carrying sulfate ions is cheap and easy to prepare, the present invention provides a process of producing dimethyltetralin in industrially quite advantageous manner.

What is claimed is:

1. A process for producing dimethyltetralin by cyclizing 5-tolyl-pent-2-ene in liquid phase in the presence of aliphatic hydrocarbon, wherein said aliphatic hydrocarbon is at least one compound selected from the group consisting of hexane, heptane, nonane, decane, cyclohexane and cyclodecane, and wherein said aliphatic hydrocarbon is used in 2 to 20 g per 1 g of 5-tolyl-pent-2-ene.

2. The process according to claim 1, wherein the cyclization of 5-tolyl-pent-2-ene is conducted in the presence of a solid acid catalyst or a liquid acid catalyst which is optionally supported on a carrier.

3. The process according to claim 3, wherein the cyclization is conducted in the presence of a liquid acid catalyst, and said liquid acid catalyst is sulfuric acid or phosphoric acid.

4. The process according to claim 2, wherein the cyclization is conducted in the presence of a solid acid catalyst, and said solid acid catalyst is at least one oxide selected from the group consisting of zeolite, silica-alumina, silica-zirconia and silica-titania.

5. The process according to claim 1, wherein the cyclization of 5-tolyl-pent-2-ene is carried out at a temperature and a pressure so as to maintain a reaction system in liquid phase.

6. The process according to claim 1, wherein a feeding rate of 5-tolyl-pent-2-ene is 0.01 to 5 hr$^{-1}$ in terms of liquid hourly space velocity.

7. The process according to claim 1, wherein the cyclization of 5-tolyl-pent-2-ene is conducted in the presence of a catalyst comprising a carrier supporting sulfate ions.

8. The process according to claim 7, wherein said carrier is at least one oxide selected from the group consisting of zirconium oxide, titanium oxide, aluminum oxide, silica and composite oxides thereof.

9. The process according to claim 7, wherein a source of sulfate ions is sulfuric acid and/or ammonium sulfate.

10. The process according to claim 7, wherein sulfate ions are supported on said carrier in 0.01 to 0.5 part by weight as SO$_4$ per 1 part by weight of said carrier.

11. The process according to claim 7, wherein the cyclization of 5-tolyl-pent-2-ene is carried out at 50 to 400° C.

12. The process according to claim 1, wherein said aliphatic hydrocarbon is at least one compound selected from the group consisting of hexane, heptane, nonane, decane and cyclohexane.

* * * * *